United States Patent [19]

Kawakami et al.

[11] Patent Number: 5,093,510
[45] Date of Patent: Mar. 3, 1992

[54] PROCESS FOR PRODUCING COPPER FORMATE

[75] Inventors: Takamasa Kawakami, Ibaraki; Ryuji Fujiura, Niigata; Kazuhiro Ando, Ibaraki; Rieko Nakano, Niigata, all of Japan

[73] Assignee: Mitsubishi Gas Chemical Co., Ltd., Tokyo, Japan

[21] Appl. No.: 622,681

[22] Filed: Dec. 5, 1990

[30] Foreign Application Priority Data

Dec. 5, 1989 [JP] Japan .................................. 1-314446

[51] Int. Cl.$^5$ .............................................. C07F 1/08
[52] U.S. Cl. ...................................... 556/114; 556/113
[58] Field of Search ........................ 556/110, 113, 114

[56] References Cited

U.S. PATENT DOCUMENTS

| | | | |
|---|---|---|---|
| 2,630,444 | 3/1953 | Fugassi et al. | 556/114 |
| 3,119,713 | 1/1964 | Hannahs | 556/114 X |
| 3,846,460 | 11/1974 | Fite, Jr. | 556/114 |

Primary Examiner—Arthur C. Prescott
Attorney, Agent, or Firm—Sughrue, Mion, Zinn, Macpeak & Seas

[57] ABSTRACT

A process for producing copper formate, which comprises subjecting methyl formate to a liquid-phase hydrolysis reaction at a temperature from 60 to 85° C. in the presence of copper carbonate.

6 Claims, No Drawings

PROCESS FOR PRODUCING COPPER FORMATE

FIELD OF THE INVENTION

The present invention relates to a process for producing copper formate. More particularly, it relates to a cost-saving process for producing copper formate which is advantageously used as a raw material for catalysts, an antibacterial agent and a raw material for the production of copper fine powder, or is used in copper plating.

BACKGROUND OF THE INVENTION

Copper formate has conventionally been utilized as a raw material for catalyst production and as an antiseptic. However, since there have been no industrial uses where copper formate is used in large quantity, the conventional method for producing copper formate is a method comprising reacting a copper compound such as copper hydroxide, copper carbonate, or the like with formic acid.

The present inventors conducted extensive investigations on the use of such copper formate, and found that the copper formate is extremely useful as a raw material for the production of copper fine powder and as a material for use in copper plating.

Those new uses of copper formate have necessitated a more cost-saving process for the production thereof which is suitable thereto, in place of the conventional copper formate-manufacturing process.

SUMMARY OF THE INVENTION

Under the above circumstances, the present inventors have made intensive studies to develop a cost-saving process for producing copper formate. As a result, it has now been found that in place of formic acid, methyl formate can be advantageously used as a formic acid source to produce copper formate. The present invention has been completed based on this finding.

Accordingly, an object of the present invention is to provide a process for producing copper formate suitable for use in various uses in an unexpensive manner.

The process for producing copper formate in accordance with the present invention comprises subjecting methyl formate to a liquid-phase hydrolysis reaction at a temperature of form 60° C. to 85° C. in the presence of copper carbonate.

In preferred embodiments of the present invention, the hydrolysis reaction is conducted using 3 to 7 equivalents of water and 0.6 to 0.8 equivalent of copper carbonate per equivalent of methyl formate; the copper carbonate is obtained by adding an alkali carbonate or an alkali hydrogen carbonate to an aqueous solution of copper sulfate, heating the resulting mixture at a temperature of from 60° C. to 85° C., thereby forming a precipitate, filtering off the precipitate to obtain a cake having a water content of from 40 to 70 wt %, and then washing the cake with water or a dilute aqueous solution of an alkali or acid; after completion of the hydrolysis reaction of methyl formate to prepare cooper formate, the copper formate is separated from the reaction mixture by removing the methyl formate remaining unreacted, methanol formed as a by-product, etc., by distillation at 60° C. to 85° C., and then concentrating the resulting reaction mixture to remove the water, thereby forming crystals of anhydrous copper formate; the crystals of anhydrous copper formate are separated from the concentrate at a temperature of from 60° C. to 85° C. under the condition that the amount of the anhydrous copper formate precipitated (crystals) is 95% or less; and the anhydrous copper formate produced is such that 90% or more thereof thermally decompose at a temperature of from 160° C. to 200° C. when heated in a nitrogen gas or hydrogen gas atmosphere at a heating rate of 3° C./min.

DETAILED DESCRIPTION OF THE INVENTION

Methyl formate has recently come to be produced at low cost by the gas-phase dehydrogenation of methanol. The methyl formate used in the present invention is not particularly required to have a high purity, and a crude methyl formate product containing methanol and water can also be used in the present invention.

The copper carbonate used in the present invention is produced by the conventional method comprising reacting a copper compound selected from various kinds of copper compounds with an alkali carbonate or an alkali hydrogen carbonate, and includes copper carbonate, basic copper carbonate, or a mixture thereof. If copper carbonate containing impurities originally contained in raw materials for the copper carbonate or in the reaction mixture is used to produce copper formate, such impurities come into the copper formate produced depending on the production process. Therefore, it is preferred to use copper carbonate in which the contents of impurities, particularly heavy metals, halogens, sulfur, and alkalis, have been reduced as much as possible.

Examples of the copper compound used to produce the copper carbonate include copper sulfate, copper chloride, and other various water-soluble copper compounds. Of these, copper sulfate is preferred in the present invention because such is easily available. As one method for producing copper carbonate from copper sulfate, sodium carbonate, sodium hydrogen-carbonate or ammonium hydrogen carbonate is added to an aqueous solution of copper sulfate in an amount 1.0 to 1.5 times the stoichiometric amount, and the resulting mixture is heated at a temperature of from 60° C. to 85° C. to form a precipitate. This precipitate is filtered off to obtain a cake having a water content of preferably from 40 to 70 wt %, more preferably from 50 to 60 wt %, and this cake is appropriately washed repeatedly with water or a dilute aqueous solution of an alkali or acid to obtain copper carbonate. Thus, the amounts of impurity elements such as Na, S, etc., resulting from the raw material compounds are reduced efficiently. If the cake has a water content lower than 40 wt %, association of the copper carbonate proceeds and part of the mother liquor containing sulfuric acid radicals, alkali cations, etc., is included in the spaces among associated particles, making the washing of the cake difficult. On the other hand, water content of the cake exceeding 70 wt % is not preferred because the washing liquid should be used in a large amount. The thus-obtained cake of copper carbonate can be advantageously used as it is in the present invention although it contains 40% to 70% by weight of water.

According to the process of the present invention, the methyl formate is subjected to a liquid-phase hydrolysis reaction in the presence of the copper carbonate, thereby to produce copper formate. In the process of the present invention, formic acid formed by the hydrolysis reacts immediately with the copper carbonate to form copper formate. Therefore, the copper formate can be produced at a rate higher than that of the equilibrium-state hydrolysis of methyl formate alone. Further, the process of the present invention is advantageous in materials of the production facilities because formic acid is not handled.

Hydrolysis reaction conditions are that the amount of water is from 3 to 7 equivalents, preferably from 4 to 6 equivalents, per equivalent of methyl formate the amount of copper carbonate is from 0.6 to 0.8 equivalent, preferably from 0.7 to 0.8 equivalent, per equivalent of methyl formate, and the temperature is from 60° C. to 85° C, preferably from 70° C. to 80° C.

If the amount of water is below 3 equivalents, the hydrolysis rate becomes unpractical. If the amount of water is 4 equivalents or less per equivalent of methyl formate, the rate of hydrolysis of methyl formate tends to become low according to the amount of water. On the other hand, the amount of water exceeding 7 equivalents is not preferred because decomposition of the copper formate is accelerated greatly. If the amount of water is more than 6 equivalents, not only the rate of hydrolysis of methyl formate is not increased any more, but the copper formate begins to decompose. The amount of copper carbonate of less than 0.6 equivalent per equivalent of methyl formate is not preferred from the economical standpoint because part of the methyl formate and formic acid remains unreacted, while the amount thereof exceeding 0.8 equivalent is not preferred in that part of the copper carbonate remains unreacted. If the reaction temperature is below 60° C, the reaction disadvantageously requires much time. Reaction temperature exceeding 85° C. is not preferred because water-insoluble decomposition products are formed.

The pressure for the liquid-phase reaction is in the range of from 5 to 9 kg/cm² (gauge pressure) according to the reaction temperature.

The copper formate formed by the reaction described above can be separated by, for example, a method in which copper formate crystals are formed by concentration, filtration, etc., and the crystals are then separated and dried.

In the reaction mixture containing water, the copper formate is in an anhydrous state at a temperature higher than about 60° C, and is in a dihydrated or tetrahydrated state or a similar state at a temperature not higher than about 60° C. If water is present in a large quantity at a temperature of 60° C. or higher, the copper formate becomes unstable. At a temperature exceeding 85° C., water-insoluble decomposition products such as basic copper formate tend to form. Increasing the temperature to 90° C. or higher is not preferred.

Therefore, the following procedures are preferred to obtain copper formate in its anhydrous state. After completion of the hydrolysis reaction of methyl formate, the methyl formate remaining unreacted and by-products such as methanol are first removed by distillation at a temperature of from 60° C. to 85° C., preferably from 60° C. to 80° C., and the resulting reaction mixture is then concentrated to remove the water, thereby forming crystals of anhydrous copper formate. In the case of obtaining higher-purity anhydrous copper formate, it is preferred that the crystals be separated from the concentrate at a temperature of from 60° C. to 85° C., preferably from 60° C. to 80° C., under the condition that the amount of the anhydrous copper formate precipitated (crystals) is 95% or less.

Thermal decomposition behaviors of various copper compounds were examined by differential thermal balance analysis in which copper hydroxide, basic copper carbonate, anhydrous copper formate, and a product of the successive decomposition of copper formate, each weighing 10 mg, were heated in an $N_2$ or $H_2$ gas atmosphere at a heating rate of 3° C./min. The results obtained are shown in Table 1 with respect to the peak temperatures in calorimetric changes (endothermic or exothermic change or similar changes) and the decomposition products.

TABLE 1

| Atmosphere | $N_2$ gas | $H_2$ gas |
|---|---|---|
| Copper hydroxide | 150–160° C. endothermic; oxide | 140–170° C. exothermic; copper powder |
| Basic copper carbonate monohydrate | 250–300° C. endothermic; oxide | 130–160° C. exothermic; copper powder |
| Anhydrous copper formate | 160–190° C. slightly endothermic; copper powder | 170–200° C. slightly exothermic; copper powder |
| Decomposition product of copper formate | 200–210° C. exothermic; oxide containing copper | 200–220° C. exothermic; copper powder |

Table 1 shows that all of the copper compounds other than anhydrous copper formate decompose in a nitrogen ($N_2$ gas) atmosphere to give copper oxide or a powder mainly comprising copper oxide, and that the decomposition of those copper compounds is endothermic or exothermic. The calorimetric changes of those copper compounds are at least 10 times that of anhydrous copper formate, and in particular, the endothermic change of basic copper carbonate monohydrate which contains water of crystallization is about 100 times that of anhydrous copper formate.

Further, it is necessary for all of the copper compounds except anhydrous copper formate to heat in a reducing ($H_2$ gas) atmosphere for the formation of metallic copper powder, and the reaction in the reducing atmosphere is exothermic. The amount of the exothermic heat is at least 5 times that of anhydrous copper formate.

Table 1 further shows that the decomposition peak temperature for the copper compounds other than anhydrous copper formate and that for anhydrous copper formate are substantially different, although some of the former slightly overlap with the latter.

From the above, it can be understood that in the case where copper formate products obtained by the process of the present invention are used in various uses as described hereinabove, the products having higher purities are suitable for such uses.

For example, it can be understood that in the case of producing a copper fine powder, anhydrous copper formate can easily be thermally decomposed at predetermined temperatures to give a copper powder without undergoing calorimetric changes. It can also be understood that in the case where anhydrous copper formate is contaminated with those raw materials or products of side reactions or decomposition, the impurity copper compounds form metallic copper by the reducing power of the decomposed formic acid. However, if the amount of the compounds other than anhydrous copper formate is too large, the amount of exothermic heat accompanying the reduction reactions becomes too large and, as a result, the copper fine powder particles formed strongly agglomerate with each other due to local heating, etc., so that a copper fine powder is difficult to obtain. If the amount of those impurity compounds is even more large, the copper powder produced is such that copper oxide has been included therein.

Therefore, the copper formate produced by the process of the present invention is preferably copper formate in which the contents of ingredients other than the copper formate are low. A practical measure of this is that when 10 mg of a sample of copper formate is heated in a nitrogen or hydrogen gas atmosphere at a heating rate of 3° C./min, 90% or more of the sample is thermally decomposed within a temperature range of from 160° C. to 200° C. In order to produce high-purity copper formate, the formation and separation of copper formate should be conducted strictly under the various conditions described above.

As apparent from the above description and as will be demonstrated by the following Examples and Comparative Examples, the process of the present invention can provide high-purity copper formate at a higher rate of hydrolysis of methyl formate.

As a result, copper formate extremely suitable for use in the production of copper fine powder or in copper powder plating etc., can be produced industrially at low cost in large quantities. Therefore, the present invention is of great significance.

The present invention will be explained in more detail by reference to the following Examples and Comparative Examples, but the Examples should not be construed to be limiting the scope of the invention. In these examples, all parts and percents are by weight unless otherwise indicated.

EXAMPLE 1

In 1,200 g of water was dissolved 300 g of copper sulfate pentahydrate. To this copper sulfate solution was added with stirring a solution obtained by dissolving 165 g of sodium carbonate in 660 g of water. This mixture was heated at 80° C. for 60 minutes to proceed reaction, and then cooled.

The resulting reaction mixture was subjected to suction filtration to obtain a copper carbonate cake weighing 287 g and having a water content of 50%. This cake was washed with various washing liquids as shown in Table 2 and filtered repeatedly to obtain a cake having a water content of 50%.

127 g of water and 180 g of methyl formate were added to the cake having a water content of 50%. This mixture was heated to 80° C. with stirring and maintained at this temperature for 60 minutes at a pressure of 8 kg/cm². The resulting reaction mixture was concentrated at 80° C. under reduced pressure until the amount of the copper formate precipitated became 90%. The crystals were separated, washed with 80° C. hot water, and then dried under reduced pressure) thereby obtaining crystals of anhydrous copper formate.

The results obtained are shown in Table 2.

TABLE 2

| | Run No. | | |
|---|---|---|---|
| | 1 | 2 | 3 |
| Washing of copper carbonate cake | | | |
| 1st washing | water 700 ml | (a) 700 ml | (b) 700 ml |
| 2nd washing | water 700 ml | water 700 ml | water 700 ml |
| 3rd washing | water 700 ml | water 700 ml | water 700 ml |
| Impurity in copper carbonate (ppm) | Na: 1300<br>S: 540 | Na: 1100<br>S: 80 | Na: 500<br>S: 140 |

TABLE 2-continued

| | Run No. | | |
|---|---|---|---|
| | 1 | 2 | 3 |
| Copper formate | | | |
| Yield (g) | 184 | 184 | 150 |
| Impurity (ppm) | Na: 1010<br>S: 420 | Na: 850<br>S: 60 | Na: 100<br>S: 5 |

Note)
(a): 0.02% $Na_2CO_3$ aqueous solution.
(b): 0.01% $CH_3COOH$ aqueous solution.

10 mg of the crystals obtained above were heated in a nitrogen or hydrogen gas atmosphere at a heating rate of 3° C./min to determine the degree of thermal decomposition of the crystals in a temperature range of from 160° C. to 200° C. (hereinafter, referred to as "thermal decomposition degree"). As a result, the thermal decomposition degree of the crystals was found to be 100%, showing substantially no inclusion of unreacted raw material compounds or copper formate decomposition products into the crystals.

The conversion of the methyl formate in the above reaction was 80%, while in a reaction conducted under the same conditions except that copper carbonate was not present, the degree of decomposition of the methyl formate was 50%.

COMPARATIVE EXAMPLE 1

The same procedures as in Example 1 were repeated except that the reaction between the copper carbonate cake and methyl formate was conducted at a temperature of 100° C. under a pressure of 10 kg/cm², and that the reaction mixture was concentrated and dried at 100° C. until the amount of the copper formate precipitated became 100%.

The copper formate thus obtained had a thermal decomposition degree of 70% and contained 30% of water-insoluble copper formate decomposition products.

COMPARATIVE EXAMPLE 2

The same procedures as in Example 1 were repeated except that the concentration of and drying the reaction mixture were conducted at 100° C. Thus, 184 g of anhydrous copper formate was obtained.

The copper formate thus obtained had a thermal decomposition degree of 90% and contained 10% of water-insoluble copper formate decomposition products.

EXAMPLE 2

The same procedures as in Example 1 were repeated except that the amounts of the copper carbonate cake, water, and methyl formate were 258 g, 87 g, and 180 g, respectively, and that after the reaction, the reaction mixture was concentrated and dried until the amount of the copper formate precipitated became 100%. Thus, 165 g of anhydrous copper formate crystals were obtained.

The crystals thus obtained had a thermal decomposition degree of 100%, showing substantially no inclusion of unreacted raw material compounds or copper formate decomposition products into the crystals.

The conversion of the methyl formate in the above reaction was 72%, while in a reaction conducted under the same conditions except that copper carbonate was not present, the degree of decomposition of the methyl formate was 42%.

EXAMPLE 3

In 1,200 g of water was dissolved 300 g of copper sulfate pentahydrate. To this copper sulfate solution was added with stirring a solution obtained by dissolving 209 g of ammonium hydrogen carbonate in 836 g of water. The resulting mixture was heated at 65° C. for 2 hours to proceed reaction, and then cooled.

The resulting reaction mixture was subjected to suction filtration to obtain 287 g of a copper carbonate cake having a water content of 50%. This cake was washed three times with 700 ml of water to obtain a cake having a water content of 50%. The copper carbonate contained impurities of 25 ppm of sulfur (resulted from the starting materials) and 20 ppm or less of sodium (unavoidable impurity).

Using the copper carbonate cake, copper formate was prepared in the same manner as in Example 1. The crystals were dried at 80° C. under reduced pressure to obtain 184 g of crystals of anhydrous copper formate.

The thermal decomposition degree of the crystals was found to be 100%, showing substantially no inclusion of unreacted raw material compound and/or copper formate decomposition products into the crystals.

While the invention has been described in detail and with reference to specific embodiments thereof, it will be apparent to one skilled in the art that various changes and modifications can be made therein without departing from the spirit and scope thereof.

What is claimed is:

1. A process for producing copper formate, which comprises subjecting methyl formate to a liquid-phase hydrolysis reaction at a temperature from 60° C. to 85° C. in the presence of copper carbonate.

2. A process as claimed in claim 1, wherein said hydrolysis reaction is conducted using 3 to 7 equivalents of water and 0.6 to 0.8 equivalent of copper carbonate per equivalent of methyl formate.

3. A process as claimed in claim 1, wherein said copper carbonate is obtained by adding an alkali carbonate or an alkali hydrogen carbonate to an aqueous solution of copper sulfate, heating the resulting mixture at a temperature of from 60° C. to 85° C. thereby forming a precipitate, filtering off the precipitate to obtain a cake having a water content of from 40 to 70 wt %, and then washing the cake with water or a dilute aqueous solution of an alkali or acid.

4. A process as claimed in claim 1, wherein after completion of the hydrolysis reaction of methyl formate to form copper formate, the copper formate is separated from the reaction mixture by distilling off the methyl formate remaining unreacted, and methanol formed as a by-product at 60° C. to 85° C., and then concentrating the resulting reaction mixture to remove the water, thereby forming crystals of anhydrous copper formate.

5. A process as claimed in claim 4, wherein in the concentration of the reaction mixture, the crystals of anhydrous copper formate are separated from the concentrate at a temperature of from 60° C. to 85° C. under the condition that the amount of the copper formate precipitated is 95% or less, thereby obtaining high-purity anhydrous copper formate.

6. A process as claimed in claim 4, wherein said anhydrous copper formate produced is such that 90% or more thereof thermally decomposes in a temperature range of from 160° C. to 200° C. when heated in a nitrogen gas or hydrogen gas atmosphere at a heating rate of 3° C./min.

* * * * *